United States Patent
Yamamoto et al.

(10) Patent No.: US 8,251,893 B2
(45) Date of Patent: Aug. 28, 2012

(54) DEVICE FOR DISPLAYING ASSISTANCE INFORMATION FOR SURGICAL OPERATION, METHOD FOR DISPLAYING ASSISTANCE INFORMATION FOR SURGICAL OPERATION, AND PROGRAM FOR DISPLAYING ASSISTANCE INFORMATION FOR SURGICAL OPERATION

(75) Inventors: Seiji Yamamoto, Hamamatsu (JP); Susumu Terakawa, Hamamatsu (JP); Masanori Takaya, Hamamatsu (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 360 days.

(21) Appl. No.: 12/525,267

(22) PCT Filed: Jan. 9, 2008

(86) PCT No.: PCT/JP2008/050139
§ 371 (c)(1),
(2), (4) Date: Sep. 30, 2009

(87) PCT Pub. No.: WO2008/093517
PCT Pub. Date: Aug. 7, 2008

(65) Prior Publication Data
US 2010/0094085 A1    Apr. 15, 2010

(30) Foreign Application Priority Data
Jan. 31, 2007 (JP) ................. P2007-022077

(51) Int. Cl.
*A61B 1/04* (2006.01)
*A61B 1/00* (2006.01)
*A61B 5/05* (2006.01)

(52) U.S. Cl. ............ 600/109; 600/117; 600/424
(58) Field of Classification Search .......... 600/109, 600/111, 114, 117, 118, 166, 407, 424–427
See application file for complete search history.

(56) References Cited

U.S. PATENT DOCUMENTS
4,506,676 A * 3/1985 Duska ................ 600/426
(Continued)

FOREIGN PATENT DOCUMENTS
JP          9-173352         7/1997
(Continued)

OTHER PUBLICATIONS
International Search Report, Corresponding to International Application No. PCT/JP2008/050139, Mailed Feb. 19, 2008.
(Continued)

*Primary Examiner* — Philip R Smith
*Assistant Examiner* — William Chou
(74) *Attorney, Agent, or Firm* — Greenlee Sullivan P.C.

(57) ABSTRACT

A device for displaying assistance information for surgical operation 1 includes an endoscope 11, a CT device 30, an image pickup device 20, a surface shape calculating unit 43, a coordinate axis matching unit 44 that matches the shape of the patient surface by the CT device 30 and the shape of the patient surface calculated from the image, an endoscope optical axis calculating unit 45 that calculates a ray indicative of an optical axis in the image pickup direction of the endoscope 11, an intersection calculating unit 46 that calculates an intersection of the ray and the plane constituting the internal parts of the patient 60, and an outputting unit 47 that outputs the information indicative of the intersection after overlapping the information on the information indicative of the shape of the patient 60.

8 Claims, 10 Drawing Sheets

U.S. PATENT DOCUMENTS

| | | | | |
|---|---|---|---|---|
| 4,583,538 | A * | 4/1986 | Onik et al. | 606/130 |
| 4,791,934 | A * | 12/1988 | Brunnett | 600/429 |
| 5,107,839 | A * | 4/1992 | Houdek et al. | 600/411 |
| 5,494,034 | A * | 2/1996 | Schlondorff et al. | 600/425 |
| 5,531,520 | A * | 7/1996 | Grimson et al. | 382/131 |
| 5,617,857 | A * | 4/1997 | Chader et al. | 600/424 |
| 5,662,111 | A * | 9/1997 | Cosman | 600/417 |
| 5,704,897 | A * | 1/1998 | Truppe | 600/117 |
| 5,871,445 | A * | 2/1999 | Bucholz | 600/407 |
| 6,135,946 | A * | 10/2000 | Konen et al. | 600/117 |
| 6,285,902 | B1 * | 9/2001 | Kienzle et al. | 600/427 |
| 6,377,839 | B1 * | 4/2002 | Kalfas et al. | 600/426 |
| 6,490,475 | B1 * | 12/2002 | Seeley et al. | 600/426 |
| 6,675,040 | B1 * | 1/2004 | Cosman | 600/427 |
| 6,725,079 | B2 * | 4/2004 | Zuk et al. | 600/414 |
| 7,967,742 | B2 * | 6/2011 | Hoeg et al. | 600/103 |
| 2001/0027272 | A1 | 10/2001 | Saito et al. | |
| 2002/0128547 | A1 | 9/2002 | Furuhashi et al. | |
| 2003/0000535 | A1 * | 1/2003 | Galloway et al. | 128/898 |
| 2003/0130576 | A1 * | 7/2003 | Seeley et al. | 600/426 |
| 2003/0163040 | A1 * | 8/2003 | Gildenberg | 600/429 |
| 2004/0138556 | A1 * | 7/2004 | Cosman | 600/424 |
| 2004/0210105 | A1 * | 10/2004 | Hale et al. | 600/101 |
| 2005/0054895 | A1 * | 3/2005 | Hoeg et al. | 600/117 |
| 2005/0054910 | A1 * | 3/2005 | Tremblay et al. | 600/411 |
| 2005/0182295 | A1 * | 8/2005 | Soper et al. | 600/117 |
| 2005/0187432 | A1 * | 8/2005 | Hale et al. | 600/117 |
| 2007/0225553 | A1 * | 9/2007 | Shahidi | 600/103 |

FOREIGN PATENT DOCUMENTS

| | | |
|---|---|---|
| JP | 2000-350734 | 12/2000 |
| JP | 2001-204738 | 7/2001 |
| JP | 2002-263053 | 9/2002 |
| JP | 2003-254732 | 9/2003 |
| JP | 2005-278992 | 10/2005 |
| JP | 2007-209531 | 8/2007 |
| WO | WO 9107726 A1 * | 5/1991 |

OTHER PUBLICATIONS

International Preliminary Report on Patentability, Corresponding to International Application No. PCT/JP2008/050139, Mailed Oct. 1, 2009.

Search Report, Corresponding to counterpart European Application No. 08703010.2, Mailed Jan. 17, 2011 (6 pages).

Colchester et al., (1996) "Development and preliminary evaluation of VISLAN, a surgical planning and guidance system using intra-operative video imaging," *Medical Image Analysis*, 1(1):73-90.

Shahidi et al., (2002) "Implementation, Calibration and Accuracy Testing of an Image-Enhanced Endoscopy System," *IEEE Transactions on Medical Imaging*, 21(12):1524-1535.

Yamashita et al. (1999) "Real-Time 3-D Model-Based Navigation System for Endoscopic Paranasal Sinus Surgery," *IEEE Transactions on Biomedical Engineering*, 46(1):107-116.

* cited by examiner

Fig.5
(a)
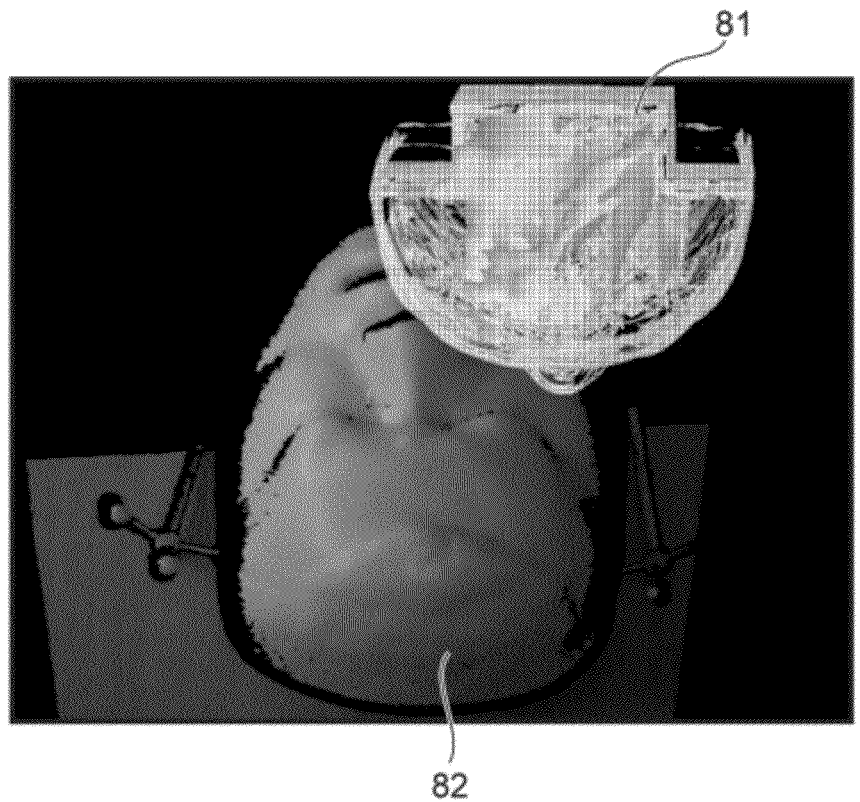
(b)
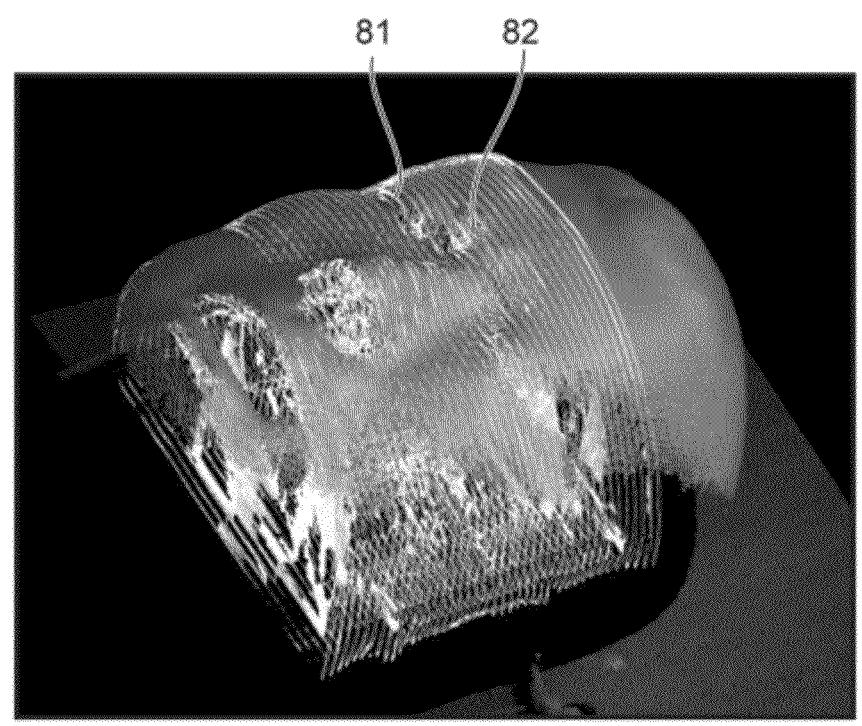

*Fig.6*
(a)
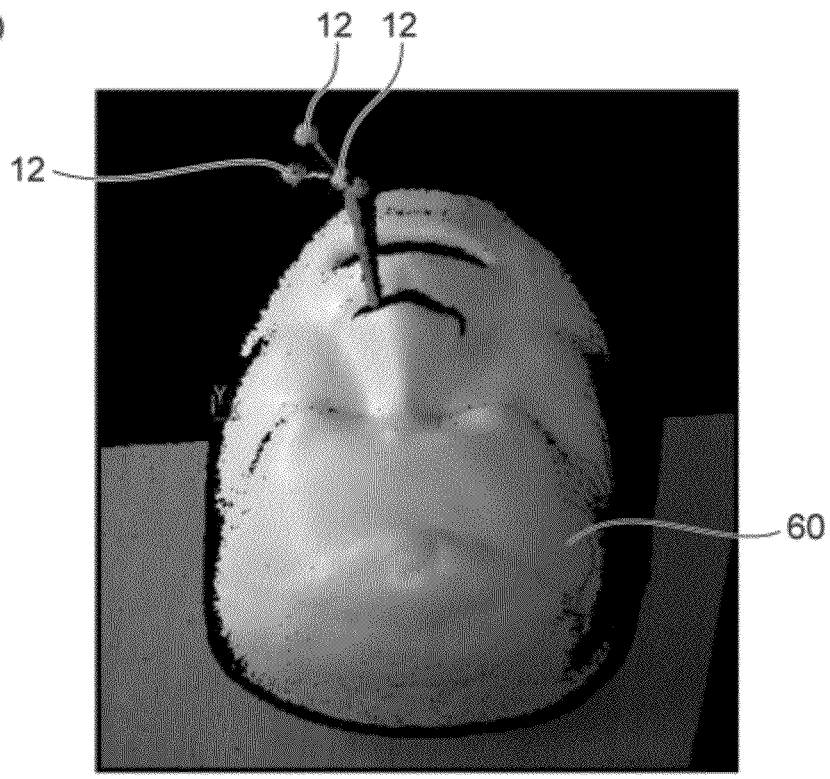
(b)
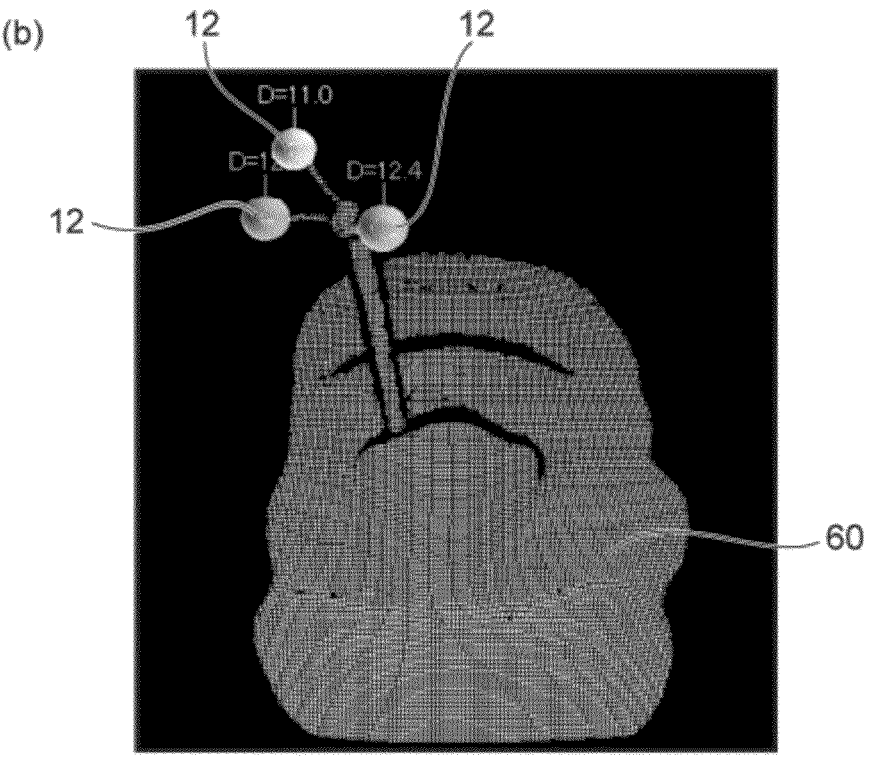

DEVICE FOR DISPLAYING ASSISTANCE INFORMATION FOR SURGICAL OPERATION, METHOD FOR DISPLAYING ASSISTANCE INFORMATION FOR SURGICAL OPERATION, AND PROGRAM FOR DISPLAYING ASSISTANCE INFORMATION FOR SURGICAL OPERATION

This application is the U.S. national stage application under 35 U.S.C. §371 of International Application No. PCT/JP2008/050139, filed Jan. 9, 2008, which claims the benefit of Japanese Application No. P2007-022077 filed Jan. 31, 2007, each of which is incorporated by reference to the extent not inconsistent with the disclosure presented herein.

TECHNICAL FIELD

The present invention relates to a device for displaying assistance information for surgical operation, a method for displaying assistance information for surgical operation, and a program for displaying assistance information for surgical operation that provide an operator etc. with information about an image picked up by an endoscope.

BACKGROUND ART

Conventionally, when a surgical instrument, such as an endoscope, is inserted into the body of a patient, surgical operation navigation (surgical operation assistance information display) that assists an operator is performed, in which the accurate position of the tip end of the surgical instrument is displayed on an image by CT (Computed Tomography) or MRI (Magnetic Resonance Imaging) photographed before the surgical operation. However, this method only displays the position of the tip end of the instrument, such as a surgical instrument and pointer, but it does not display to which part of the image before operation by CT or MRI, the region the image of which is being picked up by the endoscope corresponds.

If it is possible to confirm to which part of the image by CT etc. before operation, the region (field to be operated on displayed on the monitor of the endoscope) the image of which is being picked up by the endoscope corresponds, it is possible for an operator to confirm the position to be operated on in the direct vision by the endoscope held in his/her left hand, and to continuously carry out the operational processing by exchanging arbitrary surgical instruments with his/her right hand while recognizing which region of the image by CT etc. before operation is observed. With the arrangement, the surgical instrument does not require any special marker and it is possible to use any instrument without limitations.

As a technique that can solve the above-described problem, there is one disclosed in Patent Document 1, which displays the region observed by an endoscope on an image (by CT/MRI) before operation.

Patent document 1: Japanese Unexamined Patent Publication No. 2001-204738

DISCLOSURE OF THE INVENTION

Problem to be Solved by the Invention

However, the method described in Patent Document 1 uses an endoscope having a distance measuring means for measuring the distance between the tip end of the inserted part to be inserted into the body of a patient and the region to be operated on in the body of the patient (triangulation method using spot light irradiation, ultrasonic sensor, etc.). Accordingly, the method has a problem that a special endoscope is newly required. Further, there is a possibility that the provision of the distance measuring means may make complicated the structure of the endoscope, and the endoscope and these additional components may be damaged in the daily maintenance, such as sterilization. In a surgical operation using an endoscope, it may happen frequently that a surgical instrument, such as an aspirator, intervenes between the tip end of the endoscope and the region to be operated on in the body of a patient, and in this case, it is difficult to accurately measure the distance between the tip end of the endoscope and the region to be operated on in the body of the patient. Furthermore, when an ultrasonic sensor is used, the speed of ultrasonic wave in, for example, cerebral spinal fluid or leach in the accessory nasal sinus, is different from that in the air, and therefore, it is necessary to accurately know the speed. However, the body fluid represented by spinal fluid and leach largely differ from person to person and its composition changes when affected by the diseases, such as tumor and inflammation, and therefore, it is impossible to accurately calculate the speed of ultrasonic wave. Consequently, there is a problem that it is not possible to accurately calculate the distance between the tip end of the endoscope and the region to be operated on in the body of the patient.

The present invention has been developed to solve the above-described problems and an object thereof is to provide a device for displaying assistance information for surgical operation, a method for displaying assistance information for surgical operation, and a program for displaying assistance information for surgical operation capable of accurately displaying to which region of a patient, the part the image of which is being picked up by an endoscope corresponds using an endoscope used conventionally without the need to newly use a special endoscope.

Means for Solving the Problem

A device for displaying assistance information for surgical operation according to the present invention is characterized by comprising an endoscope that is inserted into the internal parts of a patient and which picks up an image of the internal parts, a patient shape acquiring means for acquiring information indicative of a three-dimensional shape of a plane constituting the internal parts of the patient into whom the endoscope is inserted and a surface of the patient on a first coordinate axis, an image pickup means for picking up an image of the surface of the patient when the endoscope is inserted into the patient, a surface shape calculating means for calculating information indicative of a three-dimensional shape of the surface of the patient on a second coordinate axis from the image of the surface of the patient picked up by the image pickup means, a coordinate axis matching means for matching the first coordinate axis and the second coordinate axis by matching the information indicative of the three-dimensional shape of the surface of the patient acquired by the patient shape acquiring means and the information indicative of the three-dimensional shape of the surface of the patient calculated by the surface shape calculating means, an endoscope optical axis calculating means for calculating a ray indicative of an optical axis in the image pickup direction of the endoscope on the second coordinate axis matched with the first coordinate axis by the coordinate axis matching means from the image picked up by the image pickup means, an intersection calculating means for calculating an intersection of the ray indicative of the optical axis in the image pickup direction of the endoscope calculated by the endoscope optical axis calculating means and the plane constituting the internal parts of the patient relating to the information indicative of the three-dimensional shape acquired by the patient shape acquiring means, and an outputting means for outputting the information indicative of the intersection calculated by the intersection calculating means after overlapping the information on the information indicative of the plane constituting the internal parts of the patient acquired by the patient shape acquiring means.

In the device for displaying assistance information for surgical operation according to the present invention, the information indicative of the three-dimensional shape of the plane constituting the internal parts of the patient and the surface of the patient is acquired by CT etc. On the other hand, when the endoscope is inserted into the patient, the image of the surface of the patient is picked up. From the picked-up image, information indicative of the three-dimensional shape of the surface of the patient is calculated. Following this, the (first) coordinate axis in the information indicative of the three-dimensional shape by CT etc. and the (second) coordinate axis in the picked-up image are matched by matching the information indicative of the three-dimensional shape of the respective surfaces of the patient.

Following this, the ray indicative of the optical axis in the image pickup direction of the endoscope is calculated from the picked-up image. Then, the intersection of the ray indicative of the optical axis in the image pickup direction and the plane constituting the internal parts of the patient relating to the information indicative of the three-dimensional shape by CT etc. is calculated. This intersection indicates the point (center point) at which the endoscope is picking up an image in the information indicative of the three-dimensional shape by CT etc. This information indicative of the intersection is output after being overlapped on the information indicative of the three-dimensional shape by CT etc.

That is, as described above, with the device for displaying assistance information for surgical operation according to the present invention, it is possible to display to which region of the patient, the part the image of which is being picked up by the endoscope corresponds using only the information indicative of the three-dimensional shape of the plane constituting the internal parts of the patient and the surface of the patient by CT etc. and the image of the patient picked up from outside. Accordingly, with the device for displaying assistance information for surgical operation according to the present invention, it is possible to produce the above-mentioned display without newly using a special endoscope. In addition, with the device for displaying assistance information for surgical operation according to the present invention, it is possible to accurately produce the above-mentioned display because there is no influence of liquid, such as spinal fluid, in the body of a patient.

It is desirable for the device for displaying assistance information for surgical operation according to the present invention to further comprise a marker provided in a state of being fixed on a position in a relatively positional relationship determined in advance with respect to the image pickup direction of the endoscope, and it is desirable for the image pickup means to pick up an image of the marker as well as an image of the surface of the patient when the endoscope is inserted into the patient, and for the endoscope optical axis calculating means to calculate the three-dimensional coordinates of the marker on the second coordinate axis matched with the first coordinate axis by the coordinate axis matching means from the image of the marker picked up by the image pickup means, and to calculate a ray indicative an optical axis in the image pickup direction of the endoscope from the positional relationship between the marker and the image pickup direction of the endoscope.

According to this configuration, when the endoscope is inserted into the patient, the image of the coordinates of the marker fixed in the relatively positional relationship with respect to the surface of the patient and the image pickup direction of the endoscope is picked up. Following this, from the picked-up image, the three-dimensional coordinates of the marker are calculated and the ray indicative of the optical axis in the image pickup direction of the endoscope is calculated from the calculated image of the marker. As described above, the accurate ray can be calculated more securely by calculating the ray indicative of the optical axis in the image pickup direction of the endoscope by the use of the marker, and therefore, it is possible to produce the above-mentioned accurate display more securely.

In addition, it is required for the device for displaying assistance information for surgical operation according to the present invention only to acquire the image of the surface of the patient when the endoscope is inserted into the patient, and therefore, it is not necessarily required to comprise the endoscope as a component. That is, the device for displaying assistance information for surgical operation according to the present invention is characterized by comprising a patient shape acquiring means for acquiring information indicative of a three-dimensional shape of a plane constituting the internal parts of a patient into whom an endoscope, which is inserted into the internal parts of the patient and which picks up the image of the internal parts, is inserted and a surface of the patient on a first coordinate axis, a surface image acquiring means for acquiring the image of the surface of the patient picked up when the endoscope is inserted into the patient, a surface shape calculating means for calculating information indicative of a three-dimensional shape of a surface of the patient on a second coordinate axis from the image of the surface of the patient acquired by the surface image acquiring means, a coordinate axis matching means for matching the first coordinate axis and the second coordinate axis by matching the information indicative of the three-dimensional shape of the surface of the patient acquired by the patient shape acquiring means and the information indicative of the three-dimensional shape of the surface of the patient calculated by the surface shape calculating means, an endoscope optical axis calculating means for calculating a ray indicative of an optical axis in the image pickup direction of the endoscope on the second coordinate axis matched with the first coordinate axis by the coordinate axis matching means from the image acquired by the surface image acquiring means, an intersection calculating means for calculating an intersection of the ray indicative of the optical axis in the image pickup direction of the endoscope calculated by the endoscope optical axis calculating means and the plane constituting the internal parts of the patient relating to the information indicative of the three-dimensional shape acquired by the patient shape acquiring means, and an outputting means for outputting the information indicative of the intersection calculated by the intersection calculating means after overlapping the information on the information indicative of the plane constituting the internal parts of the patient acquired by the patient shape acquiring means.

It is desirable for the intersection calculating means to calculate, using the plane constituting the internal parts of the patient as polygon data, the intersection of each plane constituting the polygon data and the ray indicative of the optical axis in the image pickup direction of the endoscope. With this configuration, it is possible to both easily and securely calculate the intersection and to securely embody the present invention.

It is desirable for the outputting means to output also the image picked up by the endoscope, on which the information indicative of the part corresponding to the intersection is overlapped. With this configuration, it is possible to provide more convenient assistance for surgical operation because it is possible for an operator to confirm simultaneously both the content the image of which is picked up by the endoscope and the information indicating to which region of the patient, the part the image of which is being picked up corresponds.

It is desirable for the image pickup means to switch image pickup conditions between when an image to be used by the shape calculating means is picked up and when an image to be used by the endoscope optical axis calculating means is picked up. With this configuration, it is possible to appropriately switch the pickup conditions in accordance with the content in which the image picked up by the image pickup means is used, and therefore, it is made possible to provide more appropriate assistance for surgical operation.

In addition, the present invention can be described as an invention of a method for displaying assistance information for surgical operation and an invention of a program for coding a motion picture as below besides the present invention can be described as an invention of a device for displaying assistance information for surgical operation as described above. The device, method, and program belong to different categories but they are substantially one and the same invention and the same working and effect can be obtained.

That is, the method for displaying assistance information for surgical operation according to the present invention is characterized by comprising a patient shape acquiring step for acquiring information indicative of a three-dimensional shape of a plane constituting the internal parts of a patient into whom an endoscope, which is inserted into the internal parts of the patient and which picks up the image of the internal parts, is inserted and a surface of the patient on a first coordinate axis, a surface image acquiring step for acquiring the image of the surface of the patient picked up when the endoscope is inserted into the patient, a surface shape calculating step for calculating information indicative of a three-dimensional shape of a surface of the patient on a second coordinate axis from the image of the surface of the patient acquired in the surface image acquiring step, a coordinate axis matching step for matching the first coordinate axis and the second coordinate axis by matching the information indicative of the three-dimensional shape of the surface of the patient acquired in the patient shape acquiring step and the information indicative of the three-dimensional shape of the surface of the patient calculated in the surface shape calculating step, an endoscope optical axis calculating step for calculating a ray indicative of an optical axis in the image pickup direction of the endoscope on the second coordinate axis matched with the first coordinate axis in the coordinate axis matching step from the image acquired in the surface image acquiring step, an intersection calculating step for calculating an intersection of the ray indicative of the optical axis in the image pickup direction of the endoscope calculated in the endoscope optical axis calculating step and the plane constituting the internal parts of the patient relating to the information indicative of the three-dimensional shape acquired in the patient shape acquiring step, and an outputting step for outputting the information indicative of the intersection calculated in the intersection calculating step after overlapping the information on the information indicative of the plane constituting the internal parts of the patient acquired in the patient shape acquiring step.

A program for displaying assistance information for surgical operation according to the present invention is characterized by causing a computer to execute a patient shape acquiring function to acquire information indicative of a three-dimensional shape of a plane constituting the internal parts of a patient into whom an endoscope, which is inserted into the internal parts of the patient and which picks up the image of the internal parts, is inserted and a surface of the patient on a first coordinate axis, a surface image acquiring function to acquire the image of the surface of the patient picked up when the endoscope is inserted into the patient, a surface shape calculating function to calculate information indicative of a three-dimensional shape of a surface of the patient on a second coordinate axis from the image of the surface of the patient acquired by the surface image acquiring function, a coordinate axis matching function to match the first coordinate axis and the second coordinate axis by matching the information indicative of the three-dimensional shape of the surface of the patient acquired by the patient shape acquiring function and the information indicative of the three-dimensional shape of the surface of the patient calculated by the surface shape calculating function, an endoscope optical axis calculating function to calculate a ray indicative of an optical axis in the image pickup direction of the endoscope on the second coordinate axis matched with the first coordinate axis by the coordinate axis matching function from the image acquired by the surface image acquiring function, an intersection calculating function to calculate an intersection of the ray indicative of the optical axis in the image pickup direction of the endoscope calculated by the endoscope optical axis calculating function and the plane constituting the internal parts of the patient relating to the information indicative of the three-dimensional shape acquired by the patient shape acquiring function, and an outputting function to output the information indicative of the intersection calculated by the intersection calculating function after overlapping the information on the information indicative of the plane constituting the internal parts of the patient acquired by the patient shape acquiring function Effects of the Invention With the present invention, it is possible to display to which region of a patient, the part the image of which is being picked up by an endoscope corresponds using only information indicative of a three-dimensional shape of a plane constituting the internal parts of the patient and the surface of the patient by CT etc. and an image of the patient picked up from outside. Therefore, according to the present invention, it is possible to produce the above-mentioned display without newly using a special endoscope. Further, according to the present invention, it is possible to accurately produce the above-mentioned display because there is no influence of liquid, such as spinal fluid, in the body of a patient.

BRIEF DESCRIPTION OF THE DRAWINGS

FIG. 5 is a diagram showing matching processing of information indicative of a three-dimensional shape of a patient by a CT device and information indicative of a three-dimensional shape of the patient calculated from an image picked up by an image pickup device.

FIG. 6 is a diagram showing processing to calculate the three-dimensional coordinates of a marker ball from an image picked up by an image pickup device.

Figure 1:
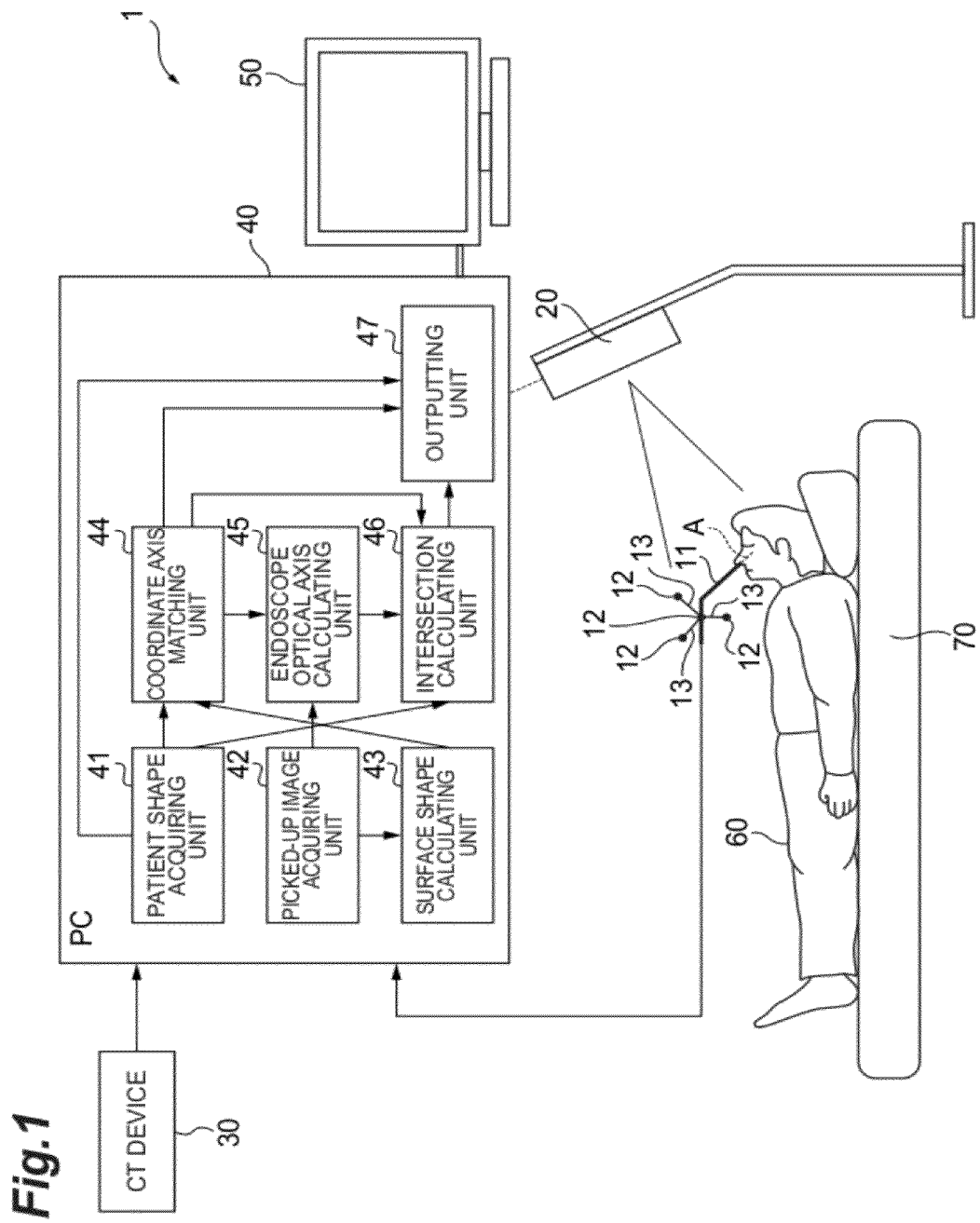
FIG. 1 is a diagram showing a configuration of a device for displaying assistance information for surgical operation according to an embodiment of the present invention.

DESCRIPTION OF THE REFERENCE SYMBOLS 1 device for displaying assistance information for surgical operation
11 endoscope
12 marker ball
20 image pickup device
30 CT device
40 PC
41 patient shape acquiring unit
42 picked-up image acquiring unit
43 surface shape calculating unit
44 coordinate axis matching unit
45 endoscope optical axis calculating unit
46 intersection calculating unit
47 outputting unit
50 monitor
60 patient
70 operating table
80 recording medium
80a program storage area
81 program for displaying assistance information for surgical operation
81a main module
81b patient shape acquiring module
81c picked-up image acquiring module
81d surface shape calculating module
81e coordinate axis matching module
81f endoscope optical axis calculating module
81g intersection calculating module
81h outputting module

BEST MODES FOR CARRYING OUT THE INVENTION

Preferred embodiments of a device for displaying assistance information for surgical operation, a method for displaying assistance information for surgical operation, and a program for displaying assistance information for surgical operation according to the present invention are explained in detail together with the drawings. In the explanation of the drawings, the same symbols are attached to the same components and duplicated explanation is omitted. The scale of dimensions (dimensional ratio) in the drawings does not necessarily coincide with that in the explanation.

FIG. 1 is a configurational diagram showing an outline of an embodiment of a device for displaying assistance information for surgical operation 1 according to the present invention. The device for displaying assistance information for surgical operation 1 is a device that provides an operator etc. with information about images picked up by an endoscope during surgical operation of a patient 60. Surgical operations in which the device for displaying assistance information for surgical operation 1 according to the present embodiment is used are, for example, those in which images are picked up by an endoscope, such as an endoscopic operation of accessory nasal sinus in an ear, nose and throat department.

As shown in FIG. 1, the device for displaying assistance information for surgical operation 1 is configured by including an endoscope 11, a marker ball 12, an image pickup device 20, a CT device 30, a PC (Personal Computer) 40, and a monitor 50.

The endoscope 11 is a device that is operated by an operator and inserted into the internal parts of the patient 60 to pick up the image of the internal parts. The endoscope 11 has an elongated shape so that it can be inserted into the body of a patient and a mechanism to pick up the image of the internal parts of the patient 60 is provided at the tip end thereof. Such a mechanism includes, for example, a lens positioned and provided so as to face a region the image of which is to be picked up and an image sensor, such as a CCD image sensor (Charge Coupled Device Image Sensor) provided in a position where the lens forms an image. The way the above-mentioned mechanism is positioned determines an image pickup direction A of the endoscope 11. Normally, the direction of the optical axis of the lens is the image pickup direction A of the endoscope 11. Information about an image picked up by the endoscope 11 is output to the PC 40 connected with the endoscope 11 via a cable. The above-mentioned endoscope 11 does not necessarily need to have a special configuration but a conventionally-used endoscope can be used.

The marker ball 12 is a marker provided in a state of being fixed on a position in a relatively positional relationship determined in advance with respect to the image pickup direction of the endoscope 11. The image of the marker ball 12 is picked up by the image pickup device 20 and the three-dimensional coordinates are found from the picked-up image. Specifically, the marker ball 12 is a spherical member different in size from one another and a plurality of the marker balls 12 is fixed on the endoscope 11 via a rod-like member 13. The size is made different from one another because each marker needs to be distinguished from one another and detected from the image picked up by the image pickup device 20.

The position in which the marker ball 12 is provided on the endoscope 11 is a position further behind the part that is inserted into the patient 60, that is, a position that is not inserted into the patient 60. The part from the part that is inserted into the internal parts of the patient 60 to the part at which the marker ball 12 is provided is formed by a hard material and cannot be bent so that the positional relationship between the marker ball 12 and the image pickup direction A of the endoscope 11 is fixed. However, it is only required to grasp the positional relationship between the image pickup direction of the endoscope 11 and the marker ball 12, and therefore, a configuration may be accepted, for example, in which only the tip end part of the endoscope 11 can be moved in a predetermined direction.

Further, it is only required for the marker provided to the endoscope 11 to be in a position in a relatively positional relationship determined in advance with respect to the image pickup direction of the endoscope 11 so that the three-dimensional coordinates can be found from the image picked up by the image pickup device 20, and therefore, the marker does not necessarily need to have a spherical shape as that of the marker ball 12 in the present embodiment. If the shape of the endoscope 11 itself is such that its three-dimensional coordinates are easily found, the shape of the endoscope 11 itself serves as a marker, and therefore, it is not necessarily required to provide the marker ball 12.

The image pickup device 20 is an image pickup means that picks up the image of the surface of the patient 60 and the marker ball 12 when the endoscope 11 is inserted into the patient 60. As shown in FIG. 1, when the endoscope 11 is inserted from the nostril of the patient 60 and the image of the head region of the patient 60 is picked up by the endoscope 11, the image pickup device 20 is provided in a position where the image of the face of the patient 60 and the marker ball 12 can be picked up. Specifically, as the image pickup device 20, for example, a CCD camera is used. The image pickup device 20 is connected with the PC 40 and transmits information about the picked-up image to the PC 40.

The image picked up by the image pickup device 20 is used to calculate the three-dimensional coordinates (three-dimensional position information) of that the image of which is picked up. It is necessary to provide also a configuration necessary for the calculation to the image pickup device 20. As a method for calculating three-dimensional coordinates of that the image of which is picked up from the image, mention is made of one that uses an optical method, and for example, a method described in Japanese Unexamined Patent Publication No. 2003-254732 can be used. When this method is used, it is necessary to further provide a device that projects a grid pattern resembling white light of natural sunlight that is emitted from xenon light in a range in which an image is picked up by the image pickup device 20.

Figure 2:
FIG. 2 is a diagram showing an image of the face of a patient, which is picked up by an image pickup device and which has three-dimensional positional information after having been subjected to information processing.

According to the method described in the Japanese Unexamined Patent Publication No. 2003-254732, it is possible to pick up an image from a distance of 90±10 cm apart with a measuring time of one second. The resolution is 0.1 to 0.6 mm. That is, it is possible to acquire a high-resolution color image having three-dimensional position information in one second. The white light has a luminance of about 28% of cloudy day light (outside) and three-dimensional position information can be safely acquired without the need to use a laser etc. An example of a high-resolution color image having three-dimensional position information is shown in FIG. 2, which is obtained by picking up the image of the face of the patient 60 and performing information processing using this method.

The CT device 30 is a patient shape acquiring means for acquiring information indicative of a three-dimensional shape of the plane constituting the internal parts of the patient 60 into whom the endoscope 11 is inserted and the surface of the patient 60. The plane that constitutes the patient 60 into whom the endoscope 11 is inserted is, for example, a plane that constitutes the accessory nasal sinus when the endoscope 11 is inserted into the accessory nasal sinus of the patient 60. The surface of the patient 60 is the face of the patient 60 in the above-mentioned case. Here, the information indicative of the three-dimensional shape acquired by the CT device 30 is configured by, for example, holding information indicative of a three-dimensional shape for each coordinate with respect to a predetermined coordinate axis set in advance in the CT device 30. This coordinate axis is a first coordinate axis. That is, the information indicative of the three-dimensional shape of the patient 60 by the CT device 30 is information on the first coordinate axis.

Figure 3:
FIG. 3 is a diagram showing a CT image acquired by a CT device.

The CT device 30 scans an object using radiation etc. and configures images (CT images) of the inner structure processed using a computer and cut into round slices at regular intervals (for example, 1 mm) as information indicative of the three-dimensional shape of the patient 60, and an already existing CT device can be used. An example of a CT image is shown in FIG. 3. The CT device 30 is connected with the PC 40 and transmits information indicative of the three-dimensional shape of the patient 60 to the PC 40. The CT device 30 does not need to be installed in the same position as that of the image pickup device 20 and normally, the image pickup by the image pickup device 20 and the acquisition of information indicative of the three-dimensional shape by the CT device 30 are performed separately. To configure information indicative of a three-dimensional shape from a CT image, for example, a method described in Japanese Unexamined Patent Publication No. 2005-278992 can be used.

It is required for the device for displaying assistance information for surgical operation 1 only to acquire information indicative of the three-dimensional shape including the internal parts of the patient 60, and therefore, the CT device 30 does not necessarily need to be used as a patient shape acquiring means. For example, an MRI device may be used.

The PC 40 receives information of the image picked up by the image pickup device 20 and information indicative of the three-dimensional shape of the patient 60 acquired by the CT device 30 and performs information processing of the information. Specifically, the PC 40 is configured by hardware, such as a CPU (Central Processing Unit) and memory, and the following functions of the PC 40 are realized by the operation of these information processing devices. As shown in FIG. 1, the PC 40 comprises a patient shape acquiring unit 41, a picked-up image acquiring unit 42, a surface shape calculating unit 43, a coordinate axis matching unit 44, an endoscope optical axis calculating unit 45, an intersection calculating unit 46, and an outputting unit 47 as functional components.

The patient shape acquiring unit 41 is a means for receiving information indicative of the three-dimensional shape of the patient 60 transmitted from the CT device 30. The patient shape acquiring unit 41 outputs the received information indicative of the three-dimensional shape of the patient 60 to the coordinate axis matching unit 44, the intersection calculating unit 46, etc., as the need arises. It is not necessarily required for the device for displaying assistance information for surgical operation 1 to comprise the CT device 30 itself as a patient shape acquiring means as in the present embodiment, but it is required for the patient shape acquiring unit 41 only to receive information indicative of the three-dimensional shape of the patient 60 (image picked up, and so on, by a CT device not included in the device for displaying assistance information for surgical operation 1).

The picked-up image acquiring unit 42 is a means for receiving information about an image picked up by the image pickup device 20 and transmitted. That is, the picked-up image acquiring unit 42 is a surface image acquiring means for acquiring an image of the surface of the patient picked up by the image pickup device 20 when the endoscope 11 is inserted into the patient 60. The picked-up image acquiring unit 42 outputs the received image to the surface shape calculating unit 43, the endoscope optical axis calculating unit 45, etc.

The surface shape calculating unit 43 is a surface shape calculating means for calculating information indicative of the three-dimensional shape of the surface of the patient 60 from the image of the surface of the patient 60 picked up by the image pickup device 20.

The surface of the patient 60 is the face of the patient 60 in the case of the present embodiment. As a method for calculating a three-dimensional shape from an image, for example, the method described in Japanese Unexamined Patent Publication No. 2003-254732 described above can be used. The information indicative of the three-dimensional shape acquired by the surface shape calculating unit 43 is calculated by, for example, configuring information indicative of a three-dimensional shape for each coordinate with respect to a predetermined coordinate axis set in advance in the surface shape calculating unit 43. This coordinate axis is a second coordinate axis, different from the above-described first coordinate axis. That is, the information indicative of the three-dimensional shape of the patient 60 by the image picked up by the image pickup device 20 is information on the second coordinate axis. The surface shape calculating unit 43 outputs the calculated information indicative of the three-dimensional shape of the surface of the patient 60 to the coordinate axis matching unit 44.

The coordinate axis matching unit 44 is a coordinate axis matching means for matching the first coordinate axis and the second coordinate axis by matching the information indicative of the three-dimensional shape of the surface of the patient 60 acquired by the patient shape acquiring unit 41 and the information indicative of the surface of the patient 60 calculated by the surface shape calculating unit 43. That is, the coordinate axis matching unit 44 is a means for enabling processing of the information indicative of the three-dimensional shape by the CT device 30 and the information indicative of the three-dimensional shape calculated from the image picked up by the image pickup device 20 on the same coordinate axis.

Specifically, the coordinate axis matching unit 44 matches the coordinate axes by matching the position of the face of the patient 60 in the information indicative of the three-dimensional shape by the CT device 30 with that in the information indicative of the three-dimensional shape calculated from the image picked up by the image pickup device 20. The processing to match the coordinate axes is performed by the use of, for example, a pattern matching method, and as a result of the processing, a function is calculated, which transforms one of the first coordinate axis and the second coordinate axis into the other coordinate axis. The coordinate axis matching unit 44 outputs the function to transform coordinate axis etc., which is calculated as a result of matching of the coordinate axes, to the endoscope optical axis calculating unit 45, the intersection calculating unit 46, the outputting unit 47, etc., as the need arises. After the above-mentioned processing to match coordinate axes, the above-mentioned function etc. is applied to information indicative of the three-dimensional shape in the endoscope optical axis calculating unit 45, the intersection calculating unit 46, the outputting unit 47, etc., and thereby, the information indicative of the three-dimensional shape by the CT device 30 and the information indicative of the three-dimensional shape calculated from the image picked up by the image pickup device 20 are processed on the same coordinate axis.

The endoscope optical axis calculating unit 45 is an endoscope optical axis calculating means for calculating the three-dimensional coordinates of the marker ball 12 on the coordinate axis matched by the coordinate axis matching unit 44 from the image of the marker ball 12 picked up by the image pickup device 20, and calculates a ray indicative of an optical axis in the image pickup direction A of the endoscope 11 from the positional relationship between the marker ball 12 and the image pickup direction A of the endoscope 11. The ray indicative of the optical axis in the image pickup direction A, referred to here, includes the position, which is the start point of the ray. That is, the ray indicative of the optical axis in the image pickup direction A of the endoscope 11 indicates from which point and in which direction an image is picked up. The endoscope optical axis calculating unit 45 holds in advance the information indicative of the positional relationship between the marker ball 12 and the image pickup direction A of the endoscope 11. Specifically, as information indicative of the positional relationship, for example, information is used, which specifies a predetermined position of the base and the tip end position of the endoscope 11 so that the optical axis of the endoscope 11 (ray indicative of the optical axis in the image pickup direction A) is passed the two points and which indicates the positional relationship between the two points and the marker ball 12.

Specifically, the calculation of the ray indicative of the optical axis in the image pickup direction A of the endoscope 11 is carried out as follows. First, the endoscope optical axis calculating unit 45 calculates a three-dimensional shape and three-dimensional coordinates from the marker ball 12 picked up by the image pickup device 20 by the same method as that which calculates a three-dimensional shape in the surface shape calculating unit 43. When two or more marker balls 12 are provided, the endoscope optical axis calculating unit 45 identifies the respective marker balls 12 from, for example, the size of the marker ball 12.

Following this, the endoscope optical axis calculating unit 45 calculates a ray indicative of an optical axis in the image pickup direction A on the above-mentioned coordinate axis from the calculated three-dimensional coordinates of the marker ball 12 on the above-mentioned coordinate axis and the information indicative of the positional relationship between the marker ball 12 and the image pickup direction A of the endoscope 11. The endoscope optical axis calculating unit 45 outputs information of the calculated ray indicative of the optical axis in the image pickup direction A to the intersection calculating unit 46.

The intersection calculating unit 46 is an intersection calculating means for calculating an intersection of the ray indicative of the optical axis in the image pickup direction A of the endoscope 11, which is calculated by the endoscope optical axis calculating unit 45, and the plane constituting the internal parts of the patient 60 relating to the information indicative the three-dimensional shape acquired by the patient shape acquiring unit 41. This intersection indicates a point (center point) at which the endoscope 11 is picking up an image in the information indicative of the three-dimensional shape by the CT device 30. Specifically, using the plane constituting the internal parts of the patient 60 as polygon data, the intersection calculating unit 46 calculates an intersection of each plane constituting the polygon data and the ray indicative of the optical axis in the image pickup direction A of the endoscope 11. The calculation of an intersection will be described later in detail. The intersection calculating unit 46 outputs information about the calculated intersection to the outputting unit 47.

The outputting unit 47 is an outputting means for outputting the information indicative of the intersection calculated by the intersection calculating unit 46 to the monitor 50 after overlapping the information on a CT image, which is information indicative of the plane constituting the internal parts of the patient 60 acquired by the patient shape acquiring unit 41. In addition, the outputting unit 47 may output also an endoscope image picked up by the endoscope 11 and input to the PC 40 to the monitor 50.

The monitor 50 displays information input from the PC 40. It is possible for an operator to know which region of the internal parts of the patient 60 is being picked up by the endoscope 11 by referring to the monitor 50. The above is the configuration of the device for displaying assistance information for surgical operation 1.

Figure 4:
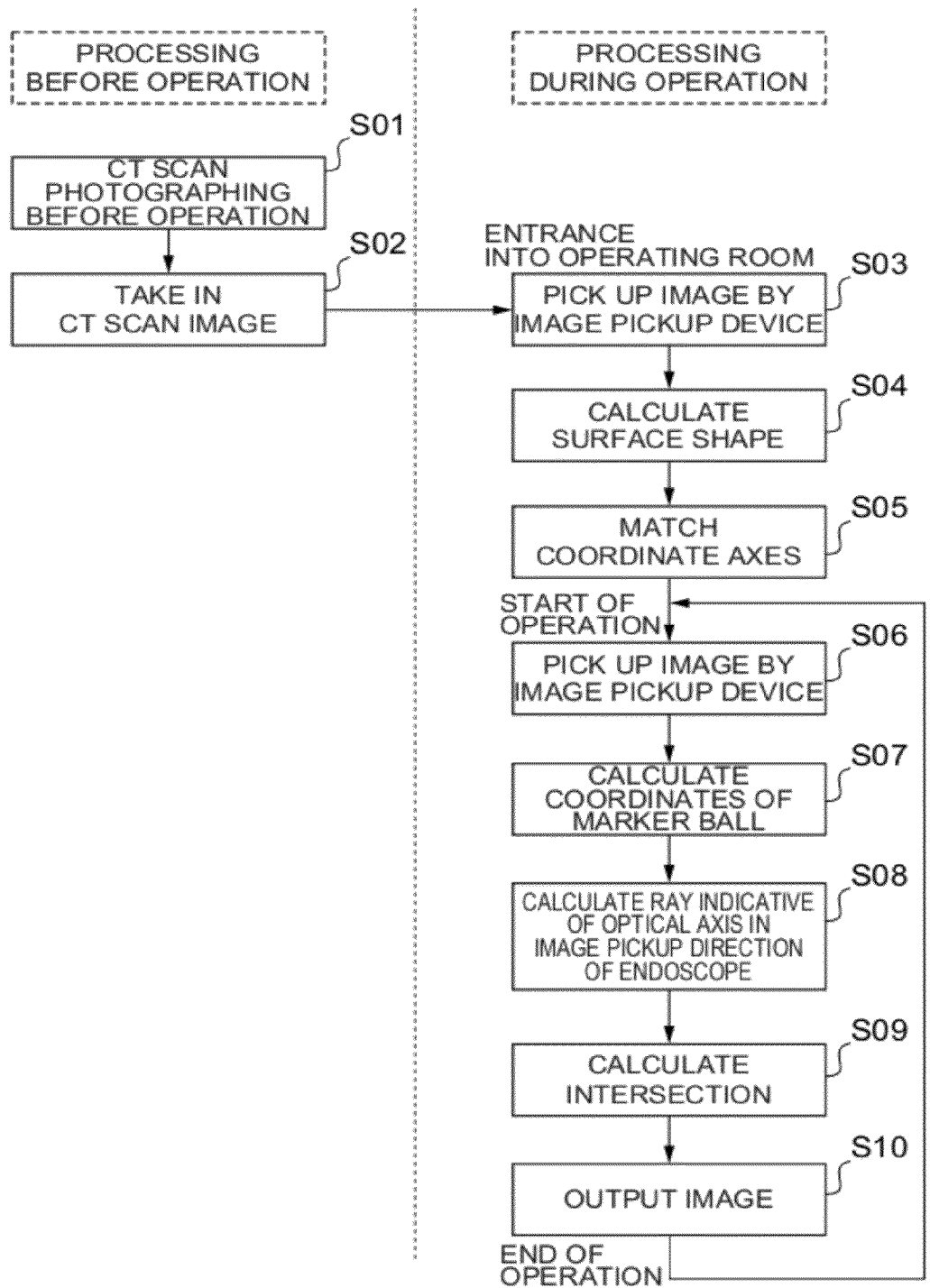
FIG. 4 is a flowchart showing processing by a device for displaying assistance information for surgical operation according to an embodiment of the present invention.

Next, the operation of the device for displaying assistance information for surgical operation 1 (method for displaying assistance information for surgical operation) is explained with reference to the flowchart in FIG. 4. This operation is, for example, carried out when medical treatment etc. is given to the patient 60 by inserting the endoscope 11 during the surgical operation. In this explanation, processing before the surgical operation and processing during the surgical operation are explained separately.

First, before the operation, CT scan photographing of the patient 60 using the CT device 30 is carried out (S01, patient shape acquiring step). This CT scan photographing is carried out for the region of the patient 60 into which the endoscope 11 is inserted. With the arrangement, information indicative of the three-dimensional shape of the face, which is the surface of the patient 60, and the plane constituting the internal parts of the patient 60 into whom the endoscope is inserted is acquired. The information indicative of the three-dimensional shape of the patient 60 acquired by carrying out the CT scan photographing by the CT device 30 is transmitted to the PC 40. In the PC 40, the patient shape acquiring unit 41 acquires the information and the information is stored in the PC 40 (S02, patient shape acquiring step). The above is the processing before the operation and performed, for example, the day before the operation.

Next, the processing during the operation is explained. First, the patient 60 is brought into an operating room and laid down face up on an operating table 70 so that the endoscope 11 can be inserted from the nostril as shown in FIG. 1. After the patient 60 is laid down and before the endoscope 11 is inserted, the image of the patient 60 laid down is picked up by the image pickup device 20 (S03, surface image acquiring step). The picked-up image is transmitted from the image pickup device 20 to the PC 40 and is received by the picked-up image acquiring unit 42 in the PC 40. The received image is output from the picked-up image acquiring unit 42 to the surface shape calculating unit 43.

The surface shape calculating unit 43 calculates information indicative of the three-dimensional shape of the face, which is the surface of the patient 60, from the image (S04, surface shape calculating step). The calculated information indicative of the three-dimensional shape of the face of the patient 60 is output from the surface shape calculating unit 43 to the coordinate axis matching unit 44. At the same timing, the information indicative of the three-dimensional shape of the patient 60 by the CT device 30, which is stored in the PC 40, is output from the patient shape acquiring unit 41 to the coordinate axis matching unit 44.

The respective coordinate axes relating to the information indicative of the three-dimensional shape of the patient 60 by the CT device 30 and the information indicative of the three-dimensional shape of the face, which is the surface of the patient 60, from the image by the image pickup device 20 do not match with each other. If the information is displayed at the same time, they are displayed in a state where information 81 by the CT device 30 is not aligned in position with information 82 by the image of the image pickup device 20, as shown in FIG. 5(a).

Here, the shape of the face in the information 81 is matched with the shape of the face in the information 82 by the coordinate axis matching unit 44 as shown in FIG. 5(b) and the coordinate axis relating to the information 81 is matched with the coordinate axis relating to the information 82 (S05, coordinate axis matching step). The matching of the shape of the face is carried out using the pattern matching technique as described above. As the regions of matching, characteristic regions are set in advance, such as the whole face and the nose and cheek of the face. The information relating to the matched coordinate axes is output from the coordinate axis matching unit 44 to the endoscope optical axis calculating unit 45, the intersection calculating unit 46, and the outputting unit 47, respectively, and the transformation etc. of the coordinate axes is performed, and after this, information processing of the three-dimensional shape is performed as the basis for the matched coordinate axes. The above is the processing before the start of the operation.

Next, the surgical operation is started and the endoscope is inserted into the patient 60 by the operator. At this time, the head of the patient 60 is prevented from moving after the processing in S03 to S05 is performed. This is because to prevent the coordinate axis from shifting. When the endoscope 11 is inserted into the patient 60, the images of the patient 60 and the marker ball 12 are picked up by the image pickup device 20 (S06, surface image acquiring step). As shown in FIG. 6(a), the picked-up image includes (the image of) the marker ball 12. The picked-up image is transmitted from the image pickup device 20 to the PC 40 and received by the picked-up image acquiring unit 42 in the PC 40. The received image is output from the picked-up image acquiring unit 42 to the endoscope optical axis calculating unit 45.

Next, the three-dimensional coordinates of the marker ball 12 are calculated from the image by the endoscope optical axis calculating unit 45 as shown in FIG. 6(b) (S07, endoscope optical axis calculating step). After that, the ray indicative of the optical axis in the image pickup direction A of the endoscope 11 on the matched coordinate axis is calculated from the three-dimensional coordinates of the marker ball 12 calculated by the endoscope optical axis calculating unit 45 based on the information indicative of the positional relationship between the marker ball 12 and the image pickup direction A of the endoscope 11, which information is held in advance (S08, endoscope optical axis calculating step).

The information of the calculated ray is output from the endoscope optical axis calculating unit 45 to the intersection calculating unit 46. At the same timing, the information indicative of the three-dimensional shape of the patient 60 by the CT device 30, which is stored in the PC 40, is output from the patient shape acquiring unit 41 to the intersection calculating unit 46. Following this, the intersection calculating unit 46 calculates an intersection of the ray indicative of the optical axis in the image pickup direction A of the endoscope 11 and the plane constituting the internal parts of the patient 60 (S09, intersection calculating step).

The calculation of the intersection is carried out as follows. First, the intersection calculating unit 46 transforms the information indicative of the three-dimensional shape of the patient 60 by the CT device 30 into polygon data. Due to this transformation, the plane constituting (the internal parts of) the patient 60 is configured by a number of, for example, triangles. Next, an intersection of each triangle and the ray indicative of the optical axis in the image pickup direction A of the endoscope 11 is calculated.

Figure 7:
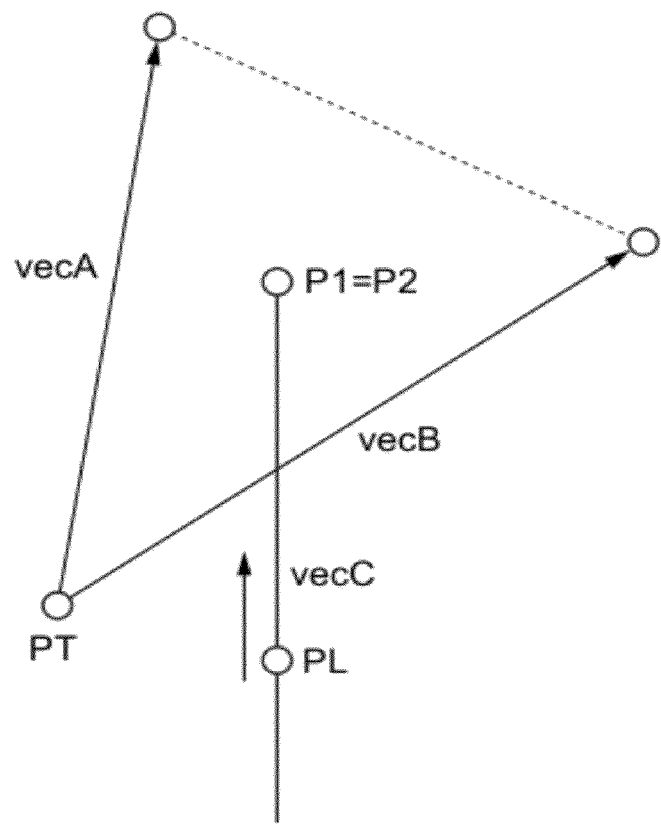
FIG. 7 is a diagram showing an intersection of a triangle constituting a plane of a patient and a ray indicative of an optical axis in the image pickup direction of an endoscope.

The calculation of the intersection is explained using FIG. 7. Let a point that serves as a reference of the triangle constituting a polygon be PT, vectors of two sides of the triangle be vec A and vec B, respectively, and two parametric variables be α, β, then, the triangle can be expressed by the following expression.

$$P1 = PT + \alpha \text{ vec } A + \beta \text{ vec } B$$

In addition, let a point that serves as a reference in the image pickup direction A of the endoscope 11 (for example, the tip end point of the endoscope 11) be PL, a vector indicative of the direction of the ray be vec C, and a parametric variable be γ, then, the image pickup direction A of the endoscope 11 can be expressed by the following expression.

$$P2 = PL + \gamma \text{ vec } C$$

Here, if both intersect with each other, then P1=P2. The condition that there exists a point that satisfies P1=P2 within the triangle is that the parametric variables satisfy the following conditions.

$0<\alpha, 0<\beta$                                                            Condition 1

$0<\alpha+\beta<1$                                           Condition 2

$\gamma>0$.                                                                   Condition 3

All points that satisfy these conditions are derived for all of the triangles constituting polygon data and the distances between all of the points and the tip end point of the endoscope 11 are calculated. The intersection with which the distance is minimum is taken as an intersection of the ray indicative of the optical axis in the image pickup direction A of the endoscope 11 and the plane constituting the internal parts of the patient 60.

Figure 8:
FIG. 8 is a diagram showing a CT image in which a point the image of which is being picked up by an endoscope is shown.

The information of the coordinates of the calculated intersection is output from the intersection calculating unit 46 to the outputting unit 47. At this timing, the CT image, which is information indicative of the plane constituting the internal parts of the patient 60, is output from the patient shape acquiring unit 41 to the outputting unit 47. The information of the intersection is overlapped on the position in accordance with the coordinates of the intersection on the CT image, which is information indicative of the plane constituting the internal parts of the patient 60, by the outputting unit 47, and then it is input to the monitor 50. The input image is displayed on the monitor 50 (S10, outputting step). Specifically, the display of the intersection is produced as, for example, a cross display 90 as shown in FIG. 8 so that it is known where the part the image of which is being picked up by the endoscope 11 is located. It is possible for an operator to know which part of the internal parts of the patient 60 is being picked up by the endoscope 11 by referring to the displayed image.

Figure 9:
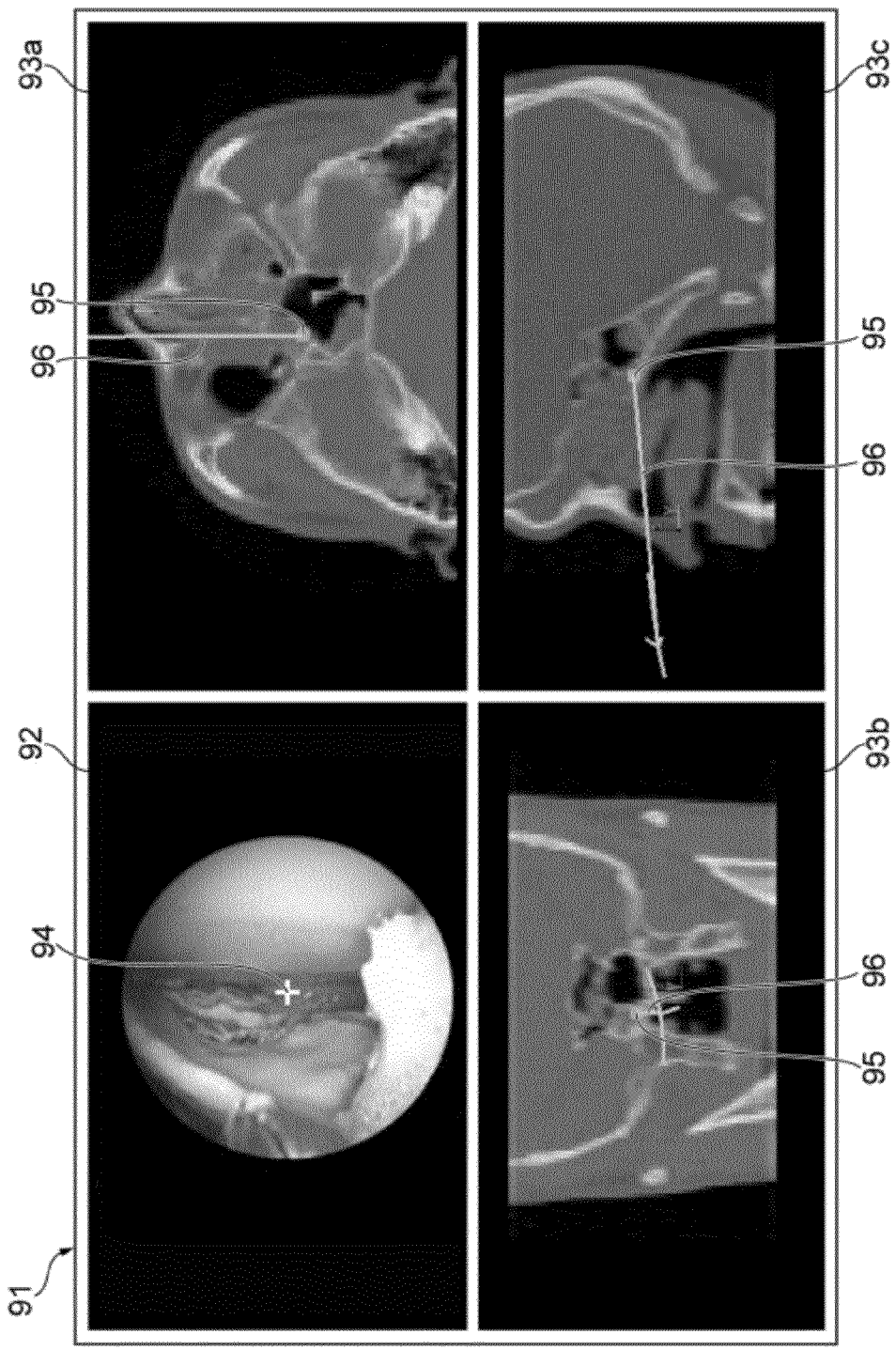
FIG. 9 is a diagram showing a CT image in which a point the image of which is being picked up by an endoscope is shown, and an image picked up by an endoscope.
Figure 10:
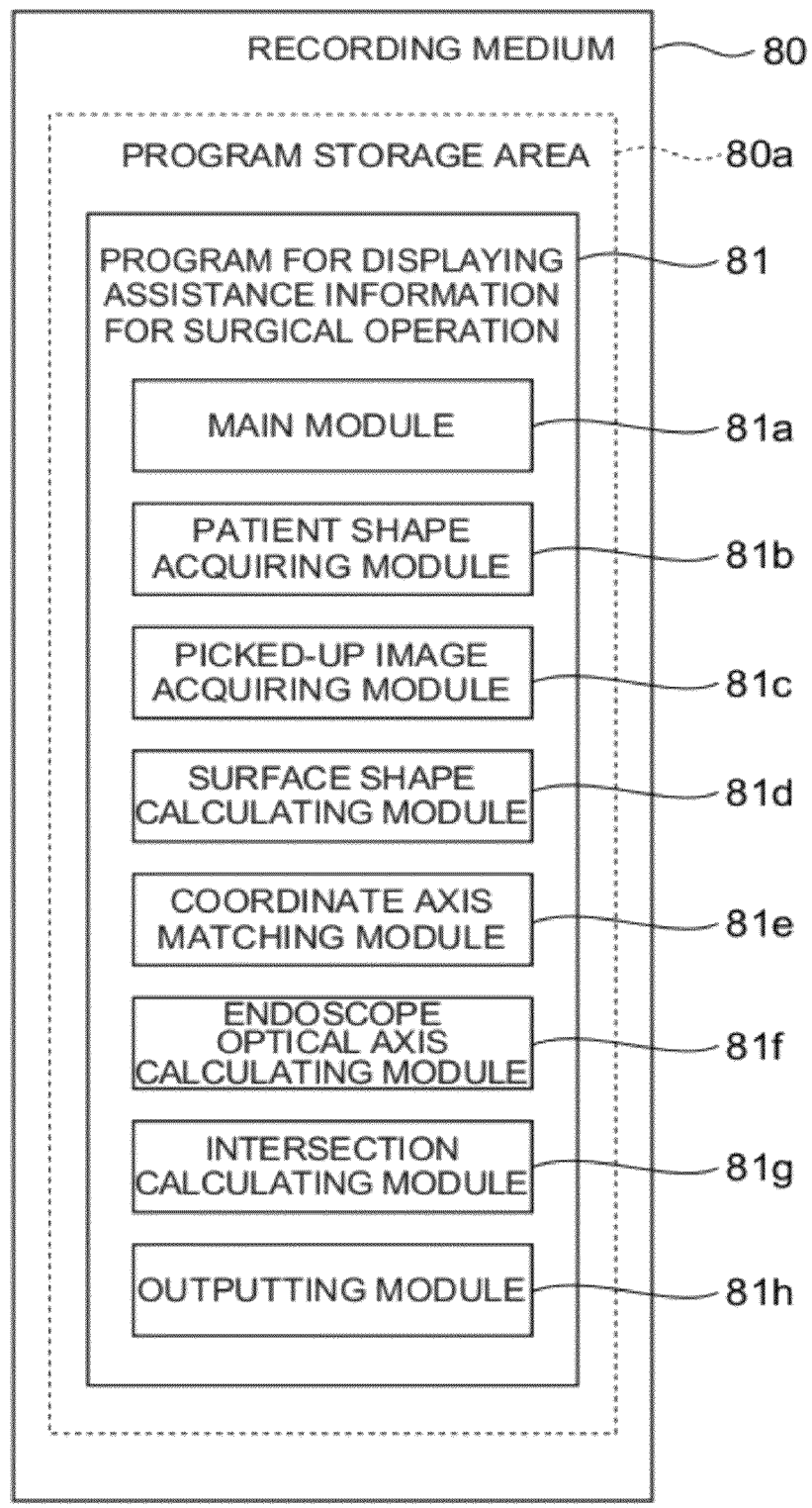
FIG. 10 is a diagram showing a configuration of a program for displaying assistance information for surgical operation according to the present invention.

In addition, it is desirable for the image picked up by the endoscope 11 to be received by the PC 40, output from the outputting unit 47 to the monitor 50, and displayed together with the above-mentioned display indicating where the part the image of which is being picked up by the endoscope 11 is located. For example, as a display example 91 shown in FIG. 9, it is recommended that an image 92 picked up by the endoscope 11 and CT images 93a to 93c indicating where the part the image of which is being picked up by the endoscope 11 is located be displayed on one screen. It is also desirable that information (for example, a cross mark) 94 indicative of the part corresponding to the intersection be overlapped on the image of the endoscope 11 at this time. The position of the information indicative of the part corresponding to the intersection in the image of the endoscope 11 is stored in advance in the outputting unit 47 in accordance with the image pickup direction of the endoscope 11, for example, the center of the image etc. It is also recommended to display two or more different sections (preferably, sections perpendicular to one another) as the CT images 93a to 93c so that an operator can easily understand the corresponding part. In FIG. 9, the CT image 93a is a transverse section, the CT image 93b is a coronal section, and the CT image 93c is a sagittal section. Further, it is desirable to display a direction (optical axis in the image pickup direction of the endoscope 11) 96 in which the endoscope 11 is inserted, in addition to the information about the intersection (shown by a rectangle 95 in a color different from that of the image) in the CT images 93a to 93c.

The processing in S06 to S10 described above is performed repeatedly at regular intervals, such as intervals of one second. Although the processing in S03 to S05 by the PC 40 is different from the processing in S06 to S10, it may also be possible to advance the processing to that in S06 and subsequent steps if, for example, the coordinate axis matching processing in S05 is performed. Further, it may also be possible to switch processing to another by the operation of an operator etc.

Even when the head of the patient 60 is moved after the positional alignment for the first time by the processing in S03 to S05, it may also be possible to perform positional alignment anew after performing the processing in S03 to S05 again. The positional alignment for the second time may be performed by the operation of an operator etc., or may be triggered by the detection of movement of the head from the comparison between the image at the time of positional alignment and the image thereafter.

As described above, it is possible for the device for displaying assistance information for surgical operation 1 according to the present embodiment to display to which region of the patient 60, the part the image of which is being picked up by the endoscope 11 corresponds using only the information indicative of the three-dimensional shape of the plane constituting the internal parts of the patient 60 by the CT device 30 and the surface of the patient, and the image of the patient 60 picked up by the image pickup device 20 from outside. Consequently, according to the device for displaying assistance information for surgical operation 1 of the present embodiment, it is possible to produce the above-mentioned display without the need to newly use a special endoscope. Further, according to the device for displaying assistance information for surgical operation 1 of the present embodiment, it is possible to accurately produce the above-mentioned display because there is no influence of liquid, such as spinal fluid, in the body of a patient. Consequently, it is possible to perform a surgical operation both safely and accurately by the use of the device for displaying assistance information for surgical operation 1 according to the present embodiment.

In addition, it is simple and easy to perform a surgical operation because there is no need to attach a mark etc. to the patient 60 at the time of CT scan photographing (S01) and it is only required to perform CT scan photographing as usual. It is not necessary to fix the patient 60 with a pin etc. for positional alignment. Even if the patient 60 is moved during operation, it is easy to perform positional alignment. Each component of the device for displaying assistance information for surgical operation 1 described above is comparatively inexpensive and can be realize at a low cost.

If the marker ball 12, which is a marker, is provided on the endoscope 11 and the ray indicative of the optical axis in the image pickup direction of the endoscope 11 is calculated using the marker as in the present embodiment, it is possible to more securely produce the above-mentioned display because an accurate ray can be calculated more securely. However, it may also be possible to calculate a ray indicative of an optical axis in the image pickup direction of the endoscope 11 without using a marker. For example, in the present embodiment, it may also be possible to calculate a shape of the endoscope 11 in the same method as that in which the surface of a patient is calculated from the image by the image pickup device 20, and then calculate a ray indicative of an optical axis in the image pickup direction of the endoscope 11 from the shape.

The present invention can be embodied if at least an image or information is input to the PC 40, and therefore, the device for displaying assistance information for surgical operation 1 does not necessarily need to comprise hardware, such as the endoscope 11, the image pickup device 20, and the CT device 30. That is, the present invention can be embodied if only each of the units 41 to 47 included in the PC 40 is provided.

In addition, if an intersection is found using the three-dimensional information of the patient 60 by the CT device 30 as polygon data as in the present embodiment, it is possible to securely calculate the intersection and therefore to securely embody the present invention.

Further, if the image itself picked up by the endoscope 11 is displayed together with the information indicating to which region of the patient 60, the part the image of which is being picked up by the image endoscope 11 corresponds, it is possible for an operator etc. to simultaneously confirm both the content of the image picked up by the endoscope 11 and the information indicating to which region of the patient 60, the part the image of which is being picked up by the endoscope 11 corresponds, and therefore, a more convenient operation assistance can be provided.

It is desirable for the image pickup device 20 to be capable of image pickup by switching image pickup conditions. Here, the image pickup conditions include, for example, the range of image pickup target, precision of image pickup, image pickup rate. Specifically, it is desirable to switch the image pickup conditions as follows between when the positional alignment of the information indicative of the three-dimensional shape of the patient 60 by the CT device 30 and the information indicative of the three-dimensional shape of the patient 60 calculated from the image by the image pickup device 20 is performed (S03 to S05, image pickup in S03) and when the image pickup direction A of the endoscope 11 is calculated (S06 to S08, image pickup in S06).

For the image pickup when positional alignment is performed, a wide range of image pickup target and high precision are required, however, high speed with respect to the time required for image pickup is not required. On the other hand, for the image pickup when the image pickup direction A of the endoscope 11 is calculated, high precision and high speed are required, however, only the recognition of the marker ball 12 is required, and therefore, the range of image pickup target may be narrow. This is because it is generally necessary to accurately measure the position of an object, such as a patient, before surgical operation, however, during the operation, it is important to both accurately and quickly measure the image pickup direction A because the operation is performed based on the image pickup direction A of the endoscope 11. When the picked-up image is used both for positional alignment and for calculation of the image pickup direction A of the endoscope 11, it is possible to make an in-between setting as described above.

As described above, if the image pickup conditions are switched in accordance with the content in which the image picked up by the image pickup device 20 is used, it is possible to provide more appropriate assistance for surgical operation, such as more accurate positional alignment or a more speedy display of the image pickup direction A of the endoscope 11.

Next, a program for displaying assistance information for surgical operation for causing a computer to execute processing to produce displays of a series of pieces of assistance information described above is explained. As shown in FIG. 9, the program for displaying assistance information for surgical operation 82 is stored in a program storage area 80a formed in a recording medium 80 included in a computer.

The program for displaying assistance information for surgical operation 81 is configured by comprising a main module 81a that totally controls display processing of assistance information for surgical operation, a patient shape acquiring module 81b, a picked-up image acquiring module 81c, a surface shape calculating module 81d, a coordinate axis matching module 81e, an endoscope optical axis calculating module 81f, an intersection calculating module 81g, and an outputting module 81h. The functions that are realized by executing the patient shape acquiring module 81b, the picked-up image acquiring module 81c, the surface shape calculating module 81d, the coordinate axis matching module 81e, the endoscope optical axis calculating module 81f, the intersection calculating module 81g, and the outputting module 81h are the same as the functions of the patient shape acquiring unit 41, the picked-up image acquiring unit 42, the surface shape calculating unit 43, the coordinate axis matching unit 44, the endoscope optical axis calculating unit 45, the intersection calculating unit 46, and the outputting unit 47, respectively, of the PC 40 described above.

In addition, the program for displaying assistance information for surgical operation 81 may have such a configuration that part or all of the programs are transmitted via a transmission medium, such as a communication line, and received and recorded (installation is included) by another device.

The invention claimed is:

1. A device for displaying assistance information for surgical operation comprising:
    an endoscope that is inserted into the internal parts of a patient and which picks up an image of the internal parts;
    a patient shape acquiring means for acquiring information indicative of a three-dimensional shape of a surface of the internal parts of the patient into whom the endoscope is inserted and an external surface of the patient on a first coordinate axis;
    a surface image pickup means for picking up an image of the external surface of the patient when the endoscope is inserted into the patient;
    a surface shape calculating means for calculating information indicative of a three-dimensional shape of an external surface of the patient on a second coordinate axis from the image of the external surface of the patient picked up by the surface image pickup means;
    a coordinate axis matching means for matching the first coordinate axis and the second coordinate axis by matching the information indicative of the three-dimensional shape of the external surface of the patient acquired by the patient shape acquiring means and the information indicative of the three-dimensional shape of the external surface of the patient calculated by the surface shape calculating means, thereby enabling processing of the information indicative of the three-dimensional shape of the patient acquired by the patient shape acquiring means and the information indicative of the three-dimensional shape of the patient calculated by the surface shape calculating means on a same coordinate axis;
    an endoscope optical axis calculating means for calculating a ray indicative of an optical axis in the image pickup direction of the endoscope on the second coordinate axis matched with the first coordinate axis by the coordinate axis matching means from the surface image picked up by the surface image pickup means;

an intersection calculating means for calculating an intersection of the ray indicative of the optical axis in the image pickup direction of the endoscope calculated by the endoscope optical axis calculating means and the surface of the internal parts of the patient relating to the information indicative of the three-dimensional shape acquired by the patient shape acquiring means; and an outputting means for outputting the information indicative of the intersection calculated by the intersection calculating means after overlapping the information on the information indicative of the surface of the internal parts of the patient acquired by the patient shape acquiring means.

2. A device for displaying assistance information for surgical operation according to claim 1, further comprising a marker fixed on a position in a relatively positional relationship determined in advance with respect to the image pickup direction of the endoscope, said marker having a three dimensional coordinates, wherein the surface image pickup means picks up an image of the marker as well as the image of the external surface of the patient when the endoscope is inserted into the patient; and the endoscope optical axis calculating means calculates the three-dimensional coordinates of the marker on the second coordinate axis matched with the first coordinate axis by the coordinate axis matching means from the image of the marker picked up by the surface image pickup means, and calculates a ray indicative of an optical axis in the image pickup direction of the endoscope from the positional relationship between the marker and the image pickup direction of the endoscope.

3. The device for displaying assistance information for surgical operation according to claim 1, wherein the image pickup means switches image pickup conditions between when an image to be used by the surface shape calculating means is picked up and when an image to be used by the endoscope optical axis calculating means is picked up.

4. A device for displaying assistance information for surgical operation comprising:

a patient shape acquiring means for acquiring information indicative of a three-dimensional shape of a surface of an internal parts of a patient into whom an endoscope, which is inserted into the internal parts of the patient and which picks up an image of the internal parts, is inserted and an external surface of the patient on a first coordinate axis;

a surface image acquiring means for acquiring the image of the external surface of the patient picked up when the endoscope is inserted into the patient;

a surface shape calculating means for calculating information indicative of a three-dimensional shape of the external surface of the patient on a second coordinate axis from the image of the surface of the patient acquired by the surface image acquiring means;

a coordinate axis matching means for matching the first coordinate axis and the second coordinate axis by matching the information indicative of the three-dimensional shape of the external surface of the patient acquired by the patient shape acquiring means and the information indicative of the three-dimensional shape of the external surface of the patient calculated by the surface shape calculating means, thereby enabling processing of the information indicative of the three-dimensional shape of the patient acquired by the patient shape acquiring means and the information indicative of the three-dimensional shape of the patient calculated by the surface shape calculating means on a same coordinate axis;

an endoscope optical axis calculating means for calculating a ray indicative of an optical axis in an image pickup direction of the endoscope on the second coordinate axis matched with the first coordinate axis by the coordinate axis matching means from the external surface image acquired by the surface image acquiring means;

an intersection calculating means for calculating an intersection of the ray indicative of the optical axis in the image pickup direction of the endoscope calculated by the endoscope optical axis calculating means and the surface of the internal parts of the patient relating to the information indicative of the three-dimensional shape acquired by the patient shape acquiring means; and an outputting means for outputting the information indicative of the intersection calculated by the intersection calculating means after overlapping the information on the information indicative of the surface of the internal parts of the patient acquired by the patient shape acquiring means.

5. The device for displaying assistance information for surgical operation according to claim 1, wherein the intersection calculating means calculates, using the surface of the internal parts of the patient as polygon data, each polygon of the polygon data having a surface, an intersection of each surface of the polygon data and the ray indicative of the optical axis in an image pickup direction of the endoscope.

6. The device for displaying assistance information for surgical operation according to claim 1, wherein the outputting means outputs also the image picked up by the endoscope.

7. A method for displaying assistance information for surgical operation comprising:

a patient shape acquiring step for acquiring information indicative of a three-dimensional shape of a surface of the internal parts of a patient into whom an endoscope, which is inserted into the internal parts of the patient and which picks up the image of the internal parts, is inserted and an external surface of the patient on a first coordinate axis;

a surface image acquiring step for acquiring an image of the external surface of the patient picked up when the endoscope is inserted into the patient;

a surface shape calculating step for calculating information indicative of a three-dimensional shape of an external surface of the patient on a second coordinate axis from the image of the external surface of the patient acquired in the surface image acquiring step;

a coordinate axis matching step for matching the first coordinate axis and the second coordinate axis by matching the information indicative of the three-dimensional shape of the external surface of the patient acquired in the patient shape acquiring step and the information indicative of the three-dimensional shape of the external surface of the patient calculated in the surface shape calculating step, thereby enabling processing of the information indicative of the three-dimensional shape of the patient acquired by the patient shape acquiring means and the information indicative of the three-dimensional shape of the patient calculated by the surface shape calculating means on a same coordinate axis;

an endoscope optical axis calculating step for calculating a ray indicative of an optical axis in the image pickup direction of the endoscope on the second coordinate axis matched with the first coordinate axis in the coordinate axis matching step from the image acquired in the surface image acquiring step;

an intersection calculating step for calculating an intersection of the ray indicative of the optical axis in the image pickup direction of the endoscope calculated in the endoscope optical axis calculating step and the surface of the internal parts of the patient relating to the information indicative of the three-dimensional shape acquired in the patient shape acquiring step; and an outputting means for outputting the information indicative of the intersection calculated in the intersection calculating step after overlapping the information on the information indicative of the surface of the internal parts of the patient acquired in the patient shape acquiring step.

8. A program for displaying assistance information for surgical operation causing a computer to execute:

a patient shape acquiring function to acquire information indicative of a three-dimensional shape of a surface of the internal parts of a patient into whom an endoscope, which is inserted into the internal parts of the patient and which picks up the image of the internal parts, is inserted and an external surface of the patient on a first coordinate axis;

a surface image acquiring function to acquire an image of the external surface of the patient picked up when the endoscope is inserted into the patient;

a surface shape calculating function to calculate information indicative of a three-dimensional shape of an external surface of the patient on a second coordinate axis from the image of the external surface of the patient acquired by the surface image acquiring function;

a coordinate axis matching function to match the first coordinate axis and the second coordinate axis by matching the information indicative of the three-dimensional shape of the external surface of the patient acquired by the patient shape acquiring function and the information indicative of the three-dimensional shape of the external surface of the patient calculated by the surface shape calculating function, thereby enabling processing of the information indicative of the three-dimensional shape of the patient acquired by the patient shape acquiring means and the information indicative of the three-dimensional shape of the patient calculated by the surface shape calculating means on a same coordinate axis;

an endoscope optical axis calculating function to calculate a ray indicative of an optical axis in the image pickup direction of the endoscope on the second coordinate axis matched with the first coordinate axis by the coordinate axis matching function from the image acquired by the surface image acquiring function;

an intersection calculating function to calculate an intersection of the ray indicative of the optical axis in the image pickup direction of the endoscope calculated by the endoscope optical axis calculating function and the surface of the internal parts of the patient relating to the information indicative of the three-dimensional shape acquired by the patient shape acquiring function; and an outputting function to output the information indicative of the intersection calculated by the intersection calculating function after overlapping the information on the information indicative of the surface of the internal parts of the patient acquired by the patient shape acquiring function.

\* \* \* \* \*